ized Patent

(12) United States Patent
Madey et al.

(10) Patent No.: US 10,032,266 B1
(45) Date of Patent: Jul. 24, 2018

(54) SIDING EVALUATION APPARATUS AND METHOD

(71) Applicant: STATE FARM MUTUAL AUTOMOBILE INSURANCE COMPANY, Bloomington, IL (US)

(72) Inventors: Taryn M. Madey, Apex, NC (US); Sharon Gibson, Carlock, IL (US); Joshua M. Mast, Bloomington, IL (US); Nathan L. Tofte, Downs, IL (US); Chad Junior Turner, Normal, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 148 days.

(21) Appl. No.: 15/085,430

(22) Filed: Mar. 30, 2016

(51) Int. Cl.
G06T 7/00 (2017.01)
G06T 7/40 (2017.01)

(52) U.S. Cl.
CPC .............. G06T 7/001 (2013.01); G06T 7/408 (2013.01); G06T 2207/10024 (2013.01)

(58) Field of Classification Search
None
See application file for complete search history.

(56) References Cited

U.S. PATENT DOCUMENTS 7,441,382 B2 * 10/2008 Beck ................... E04F 13/0841
52/543
8,885,916 B1 * 11/2014 Maurer ................ G06K 9/6202
348/137
9,079,380 B2 * 7/2015 Monteer ................. B32B 21/02
9,183,641 B2 * 11/2015 Maurer ................ G06K 9/6202
9,384,542 B1 * 7/2016 Maurer ................ G06K 9/6202
2008/0083188 A1 * 4/2008 Swanson ................... E04D 3/24
52/536
2011/0036028 A1 * 2/2011 Beck ....................... F24J 2/5203
52/173.3
2011/0060647 A1 * 3/2011 Weaver .................. G06Q 30/00
705/14.49
2011/0060648 A1 * 3/2011 Weaver .................. G06Q 30/00
705/14.49
2011/0236644 A1 * 9/2011 Garitano ............... B41M 5/0011
428/195.1
2014/0023280 A1 * 1/2014 Lin .................... G06F 17/30262
382/218

* cited by examiner

Primary Examiner — Reza Aghevli
(74) Attorney, Agent, or Firm — Marshall, Gerstein & Borun LLP; Randall G. Rueth

(57) ABSTRACT

A siding evaluation apparatus for use in identifying a characteristic of building siding is disclosed, together with methods and systems for identifying a characteristic of building siding using the siding evaluation apparatus. The siding evaluation apparatus includes a protrusion, clip, or other means for removably attaching to building siding by friction or pressure. The siding evaluation apparatus further includes a color chart holder adapted to hold a color chart for reference. The siding evaluation apparatus is attached to the siding and may be adjusted to display the color chart, which may be photographed together with a portion of the siding. Characteristics of the siding may then be determined based upon the captured photograph and a known reference area of the color chart.

20 Claims, 6 Drawing Sheets

SIDING EVALUATION APPARATUS AND METHOD

TECHNICAL FIELD

The present disclosure generally relates to a siding evaluation apparatus, system, and method for removably securing a color chart to building siding for evaluation of the building siding.

BACKGROUND

Siding is a common building covering, frequently used in wood-framed buildings to protect against water. Over time, ordinary weathering and other damage may degrade the integrity of building siding, which may then require repair or replacement. Insurers may photograph damaged building siding to make a record of its condition for claims adjustment and repairs. It is also possible to use measurements of lengths of portions of the building siding derived from an image to determine size of the building siding. For example, the methods described in Mauer et al., U.S. Pat. No. 8,885,916, may be used to identify a siding product using measurements derived from an image. Such measurements require a reference object of known length within the image. Additionally, because siding is typically installed upon the exterior of buildings, lighting conditions in which such photographs are captured can vary substantially over the course of seasons, days, or hours. This has been considered acceptable because the photographs had previously been used for reference only, and human adjusters attempt to take into consideration such changes in lighting conditions when reviewing the photographs. Such variation in lighting, exposure, and camera characteristics would be problematic if automatic processing were applied to such images, however.

In an unrelated field, color charts are used by professionals in entertainment, advertising, photography, and fine art industries. Color charts provide a set of known color patches for comparison against observed colors. Color charts frequently also provide scales of known length and dimensions for reference of distances within the image. In addition to determine size measurements of objects in captured images, color charts are typically used to check color calibration in reproductions of images or to allow a photographer to adjust camera settings prior to image capture, which may include adjusting parameters to obtain a desired color temperature and white balance. In order to use color charts for measuring objects or determining colors within an image, however, the color chart must be photographed with the image. This is typically performed by holding the color chart near an object of interest when the image is captured. This method may require an additional person to hold the color chart, however, which may further interfere with lighting conditions (e.g., by blocking light sources or by reflection).

SUMMARY

The present application discloses a siding evaluation apparatus, system, and method for use in identifying a characteristic of building siding. According to an aspect of the invention disclosed herein, the siding evaluation apparatus may comprise a color chart holder and means for removably attaching the siding evaluation apparatus to a first portion of the building siding. The means for removably attaching the siding evaluation apparatus may include using at least one of pressure or friction to hold the siding evaluation apparatus in place relative to the first portion of the building siding. The color may be adapted to hold a color chart in a manner such that the color chart and a second portion of the building siding are simultaneously visible when the siding evaluation apparatus is attached to the first portion of the building siding. In some embodiments, the color chart holder may include the color chart. Alternatively, the color chart holder may include one or more hooks or other connectors to connect to one or more of a color chart or a color chart case containing a color chart. Thus, the color chart may be removable from the color chart holder or may be integrally disposed within the color chart holder in a manner not adapted for removal.

In some embodiments, the means for removably attaching the siding evaluation apparatus to the first portion of the building siding may include a protrusion or a clip. The protrusion may be adapted to be removably inserted between rows of siding to hold the siding evaluation apparatus in place by friction or pressure. The protrusion may further include a tapered portion that is tapered to be thinner at the end of the protrusion away from the color chart holder, viz. the end of the protrusion that is inserted between the rows of siding. The tapered portion of the protrusion may have a thin end away from the color chart holder that has a thickness less than 2 millimeters and a thick end nearer the color chart holder that has a thickness greater than 2 millimeters. The clip may be adapted to receive the first portion of the building siding to hold the siding evaluation apparatus in place by friction or pressure. The clip may receive a portion of a seam of the building siding and may apply pressure to the seam to removably secure the siding evaluation apparatus. The clip may include a gap between 0.3 and 3 millimeters into which the first portion of the building siding is received.

The siding evaluation apparatus may be constructed as a single piece or may be formed of multiple pieces. When formed of multiple pieces, the siding evaluation apparatus may further be configured to allow the position of the color chart holder to be adjusted relative to the means for removably attaching the siding evaluation apparatus to the first portion of the building siding. Thus, the siding evaluation apparatus may further comprise an adjustable connector disposed between the means for removably attaching the siding evaluation apparatus to the first portion of the building siding and the color chart holder. The adjustable component may be adapted to rotate, slide, or otherwise adjust the position of the color chart holder in relation to the position of the means for removably attaching the siding evaluation apparatus to the first portion of the building siding. Thereby, the position of the color chart holder may be adjusted to display the color chart substantially parallel to the second portion of the building siding by adjusting the position of the adjustable connector between the color chart holder and the connecting portion. Whether formed as one solid piece or multiple pieces, however, any or all parts of the siding evaluation apparatus may be formed of any convenient material, such as synthetic plastics, rubbers, or solid resins.

According to a further aspect of the invention disclosed herein, the system may comprise the following: a siding evaluation apparatus adapted to removably attach to a first portion of the building siding and further adapted to hold a color chart for display in proximity to the first portion of the building siding; a color chart; an image capture device positioned to capture an image of the color chart; and a computing device communicatively connected to the image capture device, including one or more processors and a module stored in a program memory of the computing device that, when executed by the one or more processors, cause the computing device to: receive a digital image of the color chart and a second portion of the siding from the image capture device, and determine a characteristic of the building siding based upon the received digital image. The siding evaluation apparatus may be any of the embodiments of the siding evaluation apparatus as described herein. The program memory may further store executable instructions that cause the one or more processors to adjust a color profile of the digital image based upon the one or more known reference areas of the color chart.

According to a further aspect of the invention disclosed herein, the method may comprise the following: removably attaching a siding evaluation apparatus to a first portion of the building siding; capturing an image of the color chart and a second portion of the building siding using an image capture device; determining a profile for the image based upon a portion of the captured image corresponding to at least a portion of the color chart using one or more processors; and determining a characteristic of the building siding based upon the captured image and the determined profile using one or more processors. The siding evaluation apparatus may include a color chart holder adapted to hold a color chart and a connecting portion adapted to hold the siding evaluation apparatus in place by one or more connectors. The siding evaluation apparatus may also be any of the embodiments of the siding evaluation apparatus as described herein. Determining the characteristic of the building siding may include determining one or more of the following: a size associated with the building siding, a condition of the building siding, an age of the building siding, or damage to the building siding. The method may further include adjusting the position of the color chart holder to display the color chart substantially parallel to the second portion of the building siding by adjusting the position of an adjustable connector between the color chart holder and the connecting portion.

Additional aspects or embodiments of the invention are described herein. The siding evaluation apparatus, system, or method may include additional, fewer, or alternate actions, including those discussed elsewhere herein.

BRIEF DESCRIPTION OF THE DRAWINGS

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

Figure 1A:
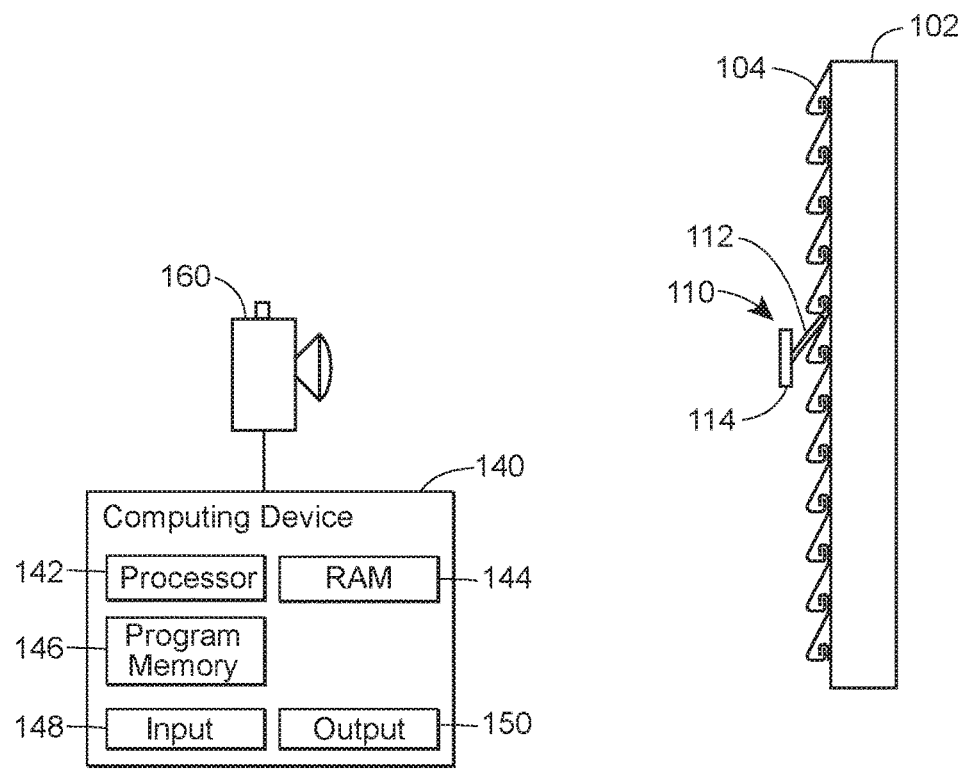
FIGS. 1A-B illustrate a side perspective view of a siding evaluation apparatus coupled to a building siding within a system including a camera communicatively connected to a computing device, which is illustrated as a block diagram, and an exemplary photograph.

FIG. 1A illustrates a side perspective view of a siding evaluation apparatus 110 coupled to a building siding 104 within a system including a camera 106 communicatively connected to a computing device 140, which is illustrated as a block diagram. The siding evaluation apparatus 110 is disposed near a building wall 102 having building siding 104. As is typical, the building siding 104 may be attached to the wall 102 such that rows (or columns, squares, shingles, etc.) of the building siding 104 overlap to form a repeating overlapping structure. In some embodiments, rows of building siding 104 may further have seams between segments or lengths of siding with the same row, where the siding segment joins flush with the next segment in the row or where the segments overlap to some degree. In preferred embodiments, the siding evaluation apparatus 110 is adapted to removably attach to the building siding 104 at one or more types of overlapping portions of the building siding 104. The siding evaluation apparatus 110 may include or hold a color chart or other known reference material to be photographed together with at least a portion of the building siding 104 using a camera 106 or other suitable image capture device. Such captures images may be used by the computing device 140 to determine characteristics of the building siding 104, as discussed below with respect to exemplary method 700 and elsewhere herein.

The siding evaluation apparatus 110 may be adapted or configured to be attached to the siding 104 by a protrusion 112 of the siding evaluation apparatus 110 or by other means. The attachment of the siding evaluation apparatus 110 may be made in such a manner that the siding evaluation apparatus 110 may be repeatedly attached to and removed from various portions of the building siding 104 or siding of other buildings. Thus, the siding evaluation apparatus 110 may be repeatedly used to provide a known reference in images of a plurality of buildings having siding by removably attaching the siding evaluation apparatus 110 to a first building, capturing an image of a portion of the siding of the first building including the siding evaluation apparatus 110, then removing the siding evaluation apparatus 110 from the first building, attaching the siding evaluation apparatus 110 to a second building having siding, capturing an image of a portion of the siding of the second building including the siding evaluation apparatus 110, and removing the siding evaluation apparatus 110 from the second building. Other means for attaching the siding evaluation apparatus 110 to the siding 104 are further discussed elsewhere herein.

The siding evaluation apparatus 110 may also include a color chart holder 114. The color chart holder 114 may be integrally formed with the protrusion 112 or other means for removably attaching the siding evaluation apparatus 110 to the building siding 104, or the color chart holder 114 may be connected thereto. If connected, the color chart holder 114 may be connected, either directly or indirectly, to another component of the siding evaluation apparatus 110 (e.g., the protrusion 112) by an adjustable connector (not shown). Such adjustable connector may include a joint, interlocking sliding connectors, a deformable or malleable interconnection, or other similar means for connecting multiple components of the siding evaluation apparatus 110 in such a manner that the position of one component (e.g., the color card holder 114) may be adjusted relative to another component (e.g., the protrusion). The color chart holder 114 may hold or contain a color chart or other known reference material, as discussed elsewhere herein, in such a manner that the color chart or other known reference material may be photographed in an image that also shows at least a portion of the building siding 104.

The computing device 140 is illustrated using a block diagram of certain key components, which are all well-known in the art. In some embodiments, the computing device 140 may be communicatively connected to the camera 106 via an external connection, such as wireless communication through a wireless network, wired communication through a cable (e.g., a USB cable) or a wired network, or other connections between the camera 106 and the computing device 140. In other embodiments, the computing device 140 may be disposed within the camera 106, or both the camera 106 and the computing device 140 may be disposed within an image capture and processing device (e.g., a smartphone, a tablet computer, a special purpose computing device having a camera, etc.). The computing device 140 may include one or more processors 142, a random access memory (RAM) 144, a program memory 146, an input 148, and an output 150, all of which may be internally connected via an address/data bus. Additional well-known components of computing systems may be included in the computing device 140 in some embodiments. The program memory 146 may store a number of software applications or routines that may be used to perform functions described further below with respect to FIG. 7, particularly at blocks 710 and 712.

Figure 1B:
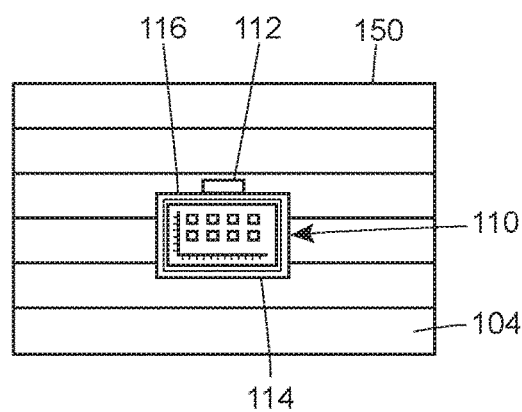

FIG. 1B illustrates an exemplary photograph using the siding evaluation apparatus 110, simultaneously showing the building siding 104 and the color chart 116 for reference. The image 150 shows a plurality of overlapping rows of the building siding 104, together with the siding evaluation apparatus 110. The image 150 shows a portion of the protrusion 112, as well as a portion of the color chart holder 114 displaying a color chart 116. The color chart 116 may include one or more known reference areas, such as color squares of known colors, vertical and horizontal scales, crosshairs, or similar reference material. The color squares may include a plurality of various colors having the same or differing areas. The vertical and horizontal scales may include ruled lines marked at known intervals or being of known length, such that distances may be determined in a standard linear measurement system (e.g., the SI system based on meters, or the system established by the U.S. National Institute of Standards and Technology). In some embodiments, the scales may be combined or implemented as alternating areas of a shape, such as alternating black and white areas of known length or width of a rectangle. The crosshairs or other similar target points may be included to serve as a basis for alignment of the color chart 116 along multiple axes (such as horizontal and vertical) in an image having multiple dimensions. In some embodiments, the crosshairs or other target points may be used to anchor or align the captured image in two or three dimensions.

Further embodiments of the siding evaluation apparatus 110 and its uses are discussed below. Such embodiments are presented as particularly useful, but the described embodiments are not intended to be limiting. Other embodiments with similar, alternative, additional, or other features will be understood by those of ordinary skill in the art. Additionally, the methods or uses described herein are exemplary only, and the siding evaluation apparatus 110 may be used for other similar uses.

Figure 2A:
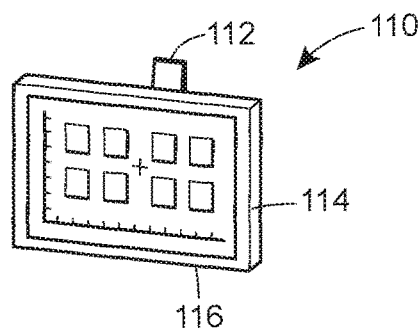
FIGS. 2A-D illustrate front perspective, side cross-sectional, and top perspective views of an exemplary embodiment of the siding evaluation apparatus for removably securing a color chart to building siding by a protrusion.
Figure 2B:
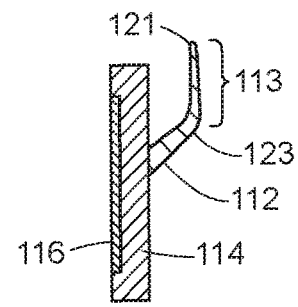
Figure 2C:
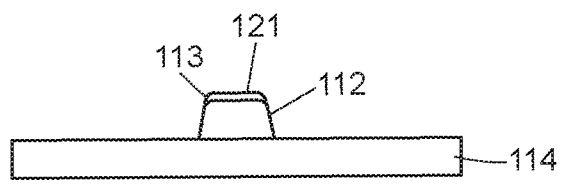

FIGS. 2A-D illustrate views of an exemplary embodiment of the siding evaluation apparatus 110 for removably attaching the color chart 116 of the color card holder 114 to building siding using the protrusion 112. The exemplary embodiment of the siding evaluation apparatus 110 illustrated in FIGS. 2A-C shows the siding evaluation apparatus 110 as having integrated or fixedly connected protrusion 112 and color chart holder 114, such that the protrusion 112 and the color chart holder 114 are formed as a single item or are connected in a manner not adapted to be adjusted. The parts are illustrated in some views as though directly joined (by adhesives or other known techniques) for clarity of the distinct parts, but the parts (i.e., the protrusion 112 and the color card holder 114) may likewise be formed as one piece. Additionally, the positioning of the parts of the siding evaluation apparatus 110 may vary in other embodiments. The illustrated embodiment further shows the color chart 116 integrated into the siding evaluation apparatus 110. In some embodiments, the color chart 116 may be removable from the color chart holder 114, such that the color chart 116 may be removed and reinserted into the color chart holder 114. In other embodiments, the color chart 116 may be integrated into or irremovably affixed to the color chart holder 114, such that removal is difficult or impossible without damage to the color chart 116 or to the color chart holder 114.

FIG. 2A illustrates a front perspective view of the exemplary embodiment of the siding evaluation apparatus 110, showing the front face of the siding evaluation apparatus 110 displaying the color chart 116. As may be seen, the protrusion 112 protrudes from or attaches to the back face of the siding evaluation apparatus 110, being the reverse side of the front face displaying the color chart 116. This allows the protrusion 112 to be inserted into the overlapping portions of the building siding 104 to removably attach the siding evaluation apparatus 110 to the building siding 104 in such a manner that the color chart 116 remains visible and may be photographed together with the building siding 104.

FIG. 2B illustrates a cross-sectional side view of the exemplary embodiment of the siding evaluation apparatus 110, showing the protrusion 112 jutting from the back face of the substantially flat color chart holder 114. The color chart 116 is shown attached to or inserted into a depression or cavity in the front face of the color chart holder 114, but it may instead be attached by adhesives or other means to a flat front side of the color chart holder 114. The protrusion 112 is shown initially departing from the back face of the color chart holder 114 at an angle between thirty and sixty degrees, although other angles may be used. The illustrated protrusion 112 then bends or curves so that a portion of the protrusion 112 is substantially parallel to the front face or back face of the color chart holder 114.

The exemplary embodiment further shows a tapered portion 113 of the protrusion 112, which extends upward and outward from the back face of the color chart holder 114. To allow the protrusion 112 to fit within a gap between overlapping segments of the building siding 104 (which gap may be pre-existing or may be caused by insertion of the protrusion 112), the tapered portion 113 may form a wedge with a thin end 121 and a thick end 123. The thin end 121 has a thickness less than the thickness of the thick end 123 along at least one axis. The thin end 121 is situated in the tapered portion 113 at the part of the protrusion 112 farthest distance along the surface of the protrusion 112 from the connection of the protrusion 112 with the remainder of the siding evaluation apparatus 110. In the illustrated embodiment, the thin end 121 is the end of the tapered portion 113 situated farthest from the area of connection between the protrusion 112 and the color chart holder 114. The thick end 123 is the end of the tapered portion 113 of the protrusion 112 that is nearer to the remainder of the siding evaluation apparatus 110 than the thin end 121. The thick end 123 is also the end of the tapered portion 113 that directly connects with the remainder of the protrusion 112, if the protrusion 112 has a non-tapered portion.

The tapered portion 113 is adapted to be inserted between overlapping sections of the building siding 104. For example, the tapered portion 113 of the protrusion 112 may be inserted between two rows of the building siding 104 where the rows overlap. The tapered portion 113 may be wedged between the two rows, such that it is able to hold the siding evaluation apparatus 110 in place by friction or pressure from the two rows. To achieve a snug fit, the tapered portion 113 of the protrusion 112 may be tapered within a range corresponding to the typical deformable gap distance between rows or other segments of the building siding 104. Such deformable gap distance represents the size of a gap that forms between segments of the building siding 104 upon application of an amount of force sufficient to cause a gap but insufficient to break or permanently deform the siding segments under ordinary conditions. Thus, when the pressure is removed by removing the protrusion 112, the siding segments will return to their previous state. It has been found by experimentation that a tapered portion 113 of the protrusion 112 having a thickness varying within the range between 0 to 5 millimeters performs well for a wide range of types of building siding 104. In preferred embodiments, the thin end 121 is less than 2 millimeters, while the thick end is greater than 2 millimeters. In particularly preferred embodiments, the thin end is approximately 0.5-1 millimeter thick and the thick end is approximately 3-4 millimeters thick. Additionally, in some embodiments, the tapered portion 113 may be between one and four centimeters in length.

The tapered portion 113 of the protrusion 112 may be tapered uniformly or non-uniformly across the length of the tapered portion 113. In preferred embodiments, the tapered portion 113 is uniformly tapered in a linear fashion between the thin end 121 and the thick end 123 to form a wedge, is flat on each side, and has a constant breadth of the tapered portion 113. The breadth of the tapered portion 113 may be measured perpendicular to the axis of the length of the tapered portion 113 (the vertical axis in FIG. 2B) and to the axis of the minimal average thickness of the tapered portion 113 (the horizontal axis in FIG. 2B), along which (horizontal) axis the thickness tapers from the thin end 121 to the thick end 123. Thus, in the cross-sectional view of FIG. 2B, the breadth would be measured along an axis perpendicular to the bisecting plane (of the image on the paper). In other embodiments, the breadth may vary in a uniform or non-uniform manner.

FIG. 2C illustrates a top perspective view of the exemplary embodiment of the siding evaluation apparatus 110, showing the protrusion 112 extending outward from the back face of the color chart holder 114. The color chart 116 is not visible in this view. The tapered portion 113 of the protrusion 112 is seen along the edge of its thin end 121. In some embodiments, the tapered portion 113 of the protrusion 112 may be substantially parallel to the face of the color chart holder 114, as illustrated. In other embodiments, the tapered portion 113 of the protrusion may instead be angled relative to the face of the color chart holder 114. In embodiments that include an adjustable connector, such adjustable connector may be disposed between the tapered portion 113 of the protrusion 112 and the remainder of the protrusion 112.

Figure 2D:
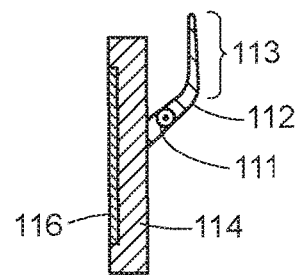

FIG. 2D illustrates a side cross-sectional view of the exemplary embodiment of the siding evaluation apparatus 110, showing an adjustable connector 111 disposed within the protrusion 112 to facilitate adjustment of the siding evaluation apparatus 110. The adjustable connector 111 may include a hinge, sliding mechanism, or other components well-known in the art. The adjustable connector 111 enables a user of the siding evaluation apparatus 110 to adjust the position of the tapered portion 113 of the protrusion 112 relative to the color chart holder 114. For example, the angle of the tapered portion 113 of the protrusion 110 relative to the color chart holder 114 may be changed by rotation of a hinge used as the adjustable connector 111. Thus, the adjustable connector 111 may be used to adjust the position of the color chart holder 114 (and, thereby, the color chart 116) relative to the position of the protrusion 112 or some portion thereof. For example, the protrusion 112 may be removably connected to the building siding 104, then the color chart holder 114 may be adjusted using the adjustable connector 111 to display the color chart 116 substantially parallel to the building siding 104.

Figure 3A:
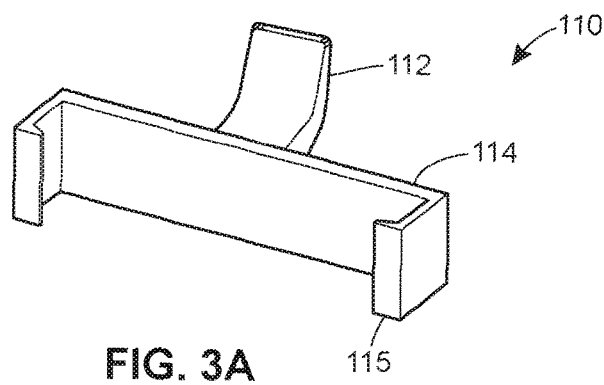
FIGS. 3A-C illustrate front perspective views and a side cross-sectional view of an exemplary embodiment of the siding evaluation apparatus for removably securing a color chart to building siding, in which the color chart is removable.
Figure 3B:
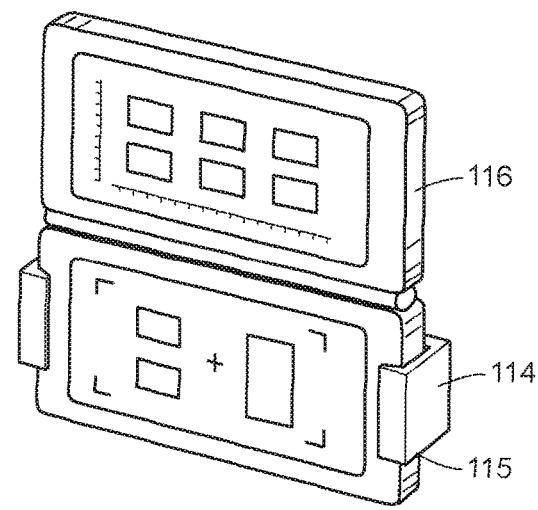
Figure 3C:
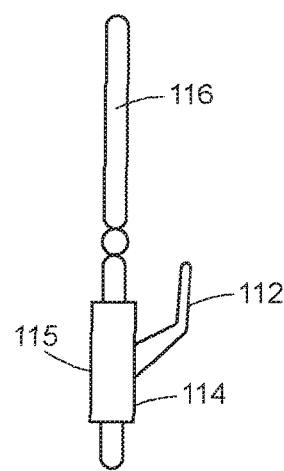

FIGS. 3A-C illustrate views of another exemplary embodiment of the siding evaluation apparatus 110, in which the color chart 114 is removable. The illustrated embodiment is otherwise similar to the embodiment discussed above, having the protrusion 112 to removably attach the siding evaluation apparatus 110 to the building siding 104. In embodiments such as the embodiment illustrated in FIGS. 3A-C, however, the color chart holder 114 is adapted to removably connect to and hold the color chart 116. Thus, the color chart holder 114 may include hooks 115 adapted to hold the color chart 116. FIG. 3A illustrates front perspective view of such an exemplary embodiment of the siding evaluation apparatus 110, showing the hooks 115 on both ends of the substantially horizontal bar forming the body of the color chart holder 114. The hooks 115 of the color chart holder 114 may be adapted to securely hold the color chart 116 in place to be photographed with the building siding 104, as discussed elsewhere herein. Although the hooks 115 are shown on the horizontal sides of the color chart holder 114, the hooks 115 may instead be positioned at other locations (e.g., the top and bottom of the color chart holder 114). Additionally, in other embodiments, the hooks 115 may be replaced by other means for removably connecting the color chart 116 to the color chart holder 114 (e.g., using one or more suction cups, supports, flaps, magnets, etc.).

The exact dimensions of the hooks 115 and other portions of the color chart holder 114 may vary across embodiments. In some embodiments, the color chart holder 114 may include extendable or retracting adjustable portions (not shown) to adjust the distance between the hooks 115 or other means for connecting the color chart 116 to the color chart holder 114. Such adjustable portions may allow the color chart holder 114 to hold a plurality of color charts 116 of different sizes or dimensions.

In some embodiments, the color chart may include a protective case 117, as illustrated in FIG. 3B. The color chart 116 may include a color card or image contained within a support structure, such as a hard plastic case. The case or other support structure may protect the color card from damage or environmental conditions. For example, the color chart 116 may be a color chart with a case, such as the ColorChecker Passport (Model No. MSCCPP) sold by X-Rite, Inc. In embodiments including a case or support structure, the hooks 115 or other means for connecting the color chart 116 to the color chart holder 114 may connect to the case or support structure of the color chart 116. As illustrated in the front perspective view of FIG. 3B and the cross-sectional side view of FIG. 3C, the hooks 115 may be configured to hold the color chart 116 by hooking to or pressing on a part of the case or support. Also as illustrated, the case or support of the color chart 116 may include a hinged connection configured in such a manner as to facilitate the opening and closing of the color chart 116 while held by the color chart holder 114. Thus, the color chart 116 may remain connected to the color chart holder 114 when opened or closed, allowing the color chart 116 to be closed to protect the one or more color cards within the case in some embodiments.

Figure 4A:
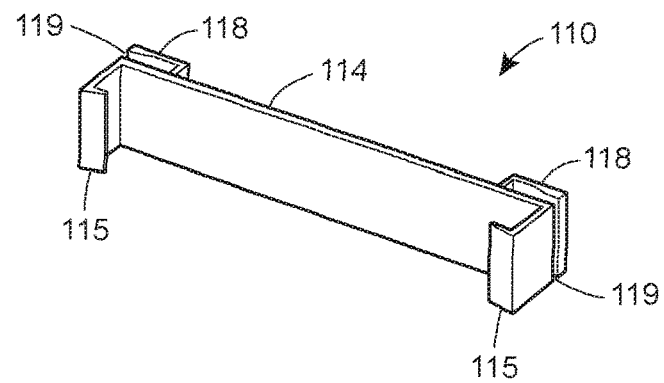
FIGS. 4A-B illustrate front perspective and top cross-sectional views of an exemplary embodiment of the siding evaluation apparatus for removably securing a color chart to building siding, in which the siding evaluation apparatus is configured to clip to a seam of the building siding.
Figure 4B:
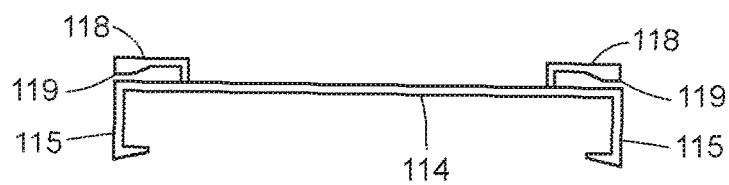

Although the embodiments described above have included the protrusion 112 for attaching the siding evaluation apparatus 110 to the building siding 110, the siding evaluation apparatus 110 may include additional or alternative means of connecting to the building siding 110 by friction or pressure. FIGS. 4A-B illustrate views of an exemplary embodiment of the siding evaluation apparatus 110 in which the siding evaluation apparatus 110 includes clips 118 configured to clip to a seam of the building siding 104. The exemplary embodiment is illustrated as having hooks 115 to connect to the color chart 116, as described above, to more clearly show the clips 118, but other types of color chart holders 114 may likewise be used in embodiments of the siding evaluation apparatus 110 having clips 118. FIG. 4A illustrates a front perspective view of the exemplary embodiment of the siding evaluation apparatus 110, showing the clips 118 attaching to the back face of the color chart holder 114. FIG. 4B illustrates a top cross-sectional view of the exemplary embodiment of the siding evaluation apparatus 110, further showing the position of the clips 118.

The one or more clips 118 may be adapted to to receive the portion of the building siding 104 to hold the siding evaluation apparatus in place. In preferred embodiments, the clips 118 may be configured to receive a portion of a seam between segments of the building siding 104, such as a seam between segments within a row of the building siding 104. The portion of the seam may be received into a gap of the clip 118. Thus, the portion of the seam received may be a first portion of the building siding 104 that overlaps a second portion of the building siding 104, where the overlapping first portion covers the overlapped second portion, which overlapped second portion is closer to the wall 102. The clips may be configured such that the portion of the seam received is substantially parallel to the color chart holder 114 and, thereby, to the color chart 116 (when include in or held by the color chart holder 114). To clip the siding evaluation apparatus 110 to the seam or other portion of the building siding 104, one or more clips 118 may be adapted to apply a pressure to the received portion of the building siding 104 when it is inserted into gap to hold the siding evaluation apparatus 110 in place relative to the building siding 104. In some preferred embodiments, the gaps of the one or more clips 118 will be between 0.3 and 3 millimeters distance when no pressure is being applied. Thus, the received portion of the building siding 104 will be held securely by the clip 118 by the application of pressure resulting from a deformation of the clip 118.

To facilitate a secure attachment, the clip 118 may be adapted to bulge, taper, or angle at the outer edge that first receives the received portion of the building siding 104 in order to create a pressure point 119. The pressure point 119 of the clip 118 may be the point where the gap is the narrowest when the clip 118 is at rest (i.e., when nothing is inserted into the clip 118) or when in use (e.g., when the received portion of the building siding 104 is inserter into the clip 118). Thus, the pressure point 119 may apply the greatest pressure to the received portion of the building siding 104 to limit slipping and to hold the siding evaluation apparatus 110 more securely in place relative to the building siding 104. In preferred embodiments using clips 118 having pressure points 119, the gaps may be between 0.5 and 2 millimeters at the pressure points 119.

Although the clip 118 is illustrated as having a gap between a portion of the clip 118 and a portion of the color chart holder 114, the clip 118 could further include multiple grasping portions that include a gap between them, such that the multiple grasping portions together exert a pressure upon the received portion of the building siding 104 when inserted between two or more of the multiple grasping portions. For example, the clip 118 may include multiple gaps between multiple grasping portions, wherein at least two gaps are of different dimensions. Thus, the clip 118 may be adapted to receive multiple types of building siding 104 of different thicknesses. Additionally, or alternatively, a plurality clips 118 may be disposed within the siding evaluation apparatus 110. Such plurality of clips 118 may include clips having gaps of different widths or different configurations or widths of pressure points 119. Such plurality of clips 118 may also be configured to permit attachment to the building siding 104 at various locations relative to the color chart holder 114.

In further embodiments, the clip 118 may include a spring or similar features adapted to allow the clip 118 to form a gap into which the received portion of the building siding 104 may be inserted and to apply pressure to the received portion of the building siding 104. In such embodiments with springs or similar features, the gap may not exist unless a pressure is applied (e.g., by a user opening the clip 118, by the insertion of the received portion of the building siding 104, etc.). When such an actively grasping clip 118 is not is use, therefore, no gap may be apparent. For example, the clip 118 may include a spring (not shown) that applies a pressure to cause the pressure point 119 to press against a portion of the color chart holder 114 unless the force applied by the spring is overcome by a user or by insertion of some material into the clip 118.

Figure 5:
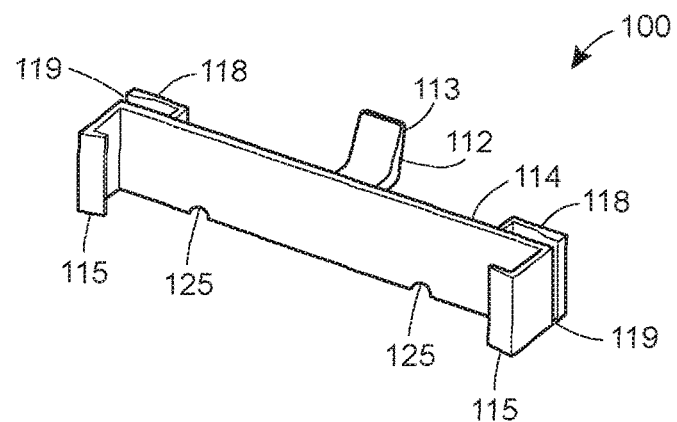
FIG. 5 illustrates a perspective view of an exemplary embodiment of the siding evaluation apparatus for removably securing a color chart to building siding, having both clips and a protrusion.

FIG. 5 illustrates a perspective view of a particularly preferred embodiment of the of the siding evaluation apparatus 110, having both a protrusion 112 and clips 118. In this exemplary illustration of the preferred embodiment, the protrusion 112 and two clips 118 protrude from the back face of the color chart holder 114. The protrusion 112 protrudes from the back face of the color chart holder 114 and curves upward in a vertical direction. The protrusion 112 also includes a tapered portion 113, as discussed elsewhere herein. The two clips 118 protrude from the back face of the color chat holder 114 such that gaps are formed between a portion of the clips 118 and a portion of the back face of the color chart holder 114. The pressure points 119 of the clips 118 are located approximately at the horizontal ends of the color chart holder 114. Also located at the horizontal ends of the color chart holder 114, two hooks 115 are located at or extend from the front face of the color chart holder 114. The hooks 115 are configured to point inward towards each other in order to securely connect to (or grasp) the color chart 116 when inserted between the hooks 115. The color chart 116 is not shown in FIG. 5 in order to better illustrate the other features. The removable color chart 116 is shown connected to the color chart holder 114 of the siding evaluation apparatus 110 in FIGS. 3B and 3C. Returning to FIG. 5, he color chart holder 114 may thus be said to be primarily horizontal, having its greatest length in that direction. The color chart holder 114 may be substantially flat along its front and back faces, excepting the hooks 115, forming a rectangular cuboid having a horizontal length greater than either its vertical height between its top and bottom faces or its thickness in depth between its front and back faces. One or more notches 125 may be added to the color chart holder 114 to aid in removing the color chart 115 from the color chart holder 114. This embodiment, like the other embodiments herein, is exemplary only, and other embodiments having additional, fewer, alternative, or similar features fall within the scope of the invention described herein.

Figure 6A:
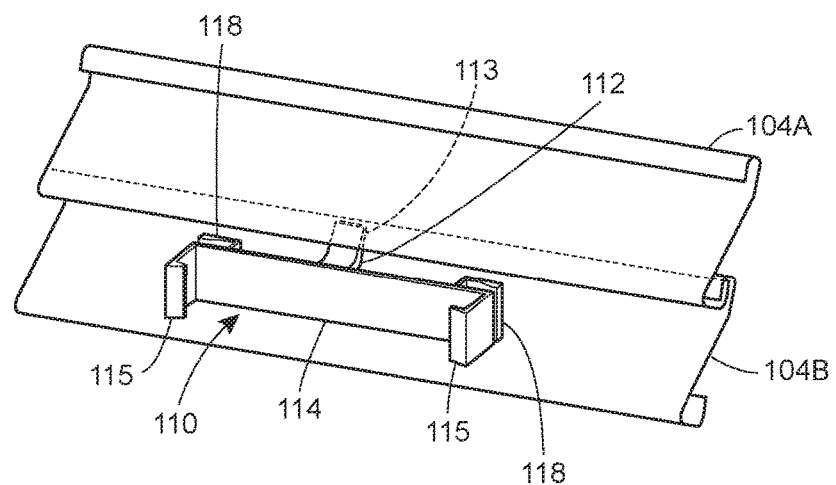
FIGS. 6A-B illustrate perspective views of the siding evaluation apparatus removably attached to building siding.
Figure 6B:
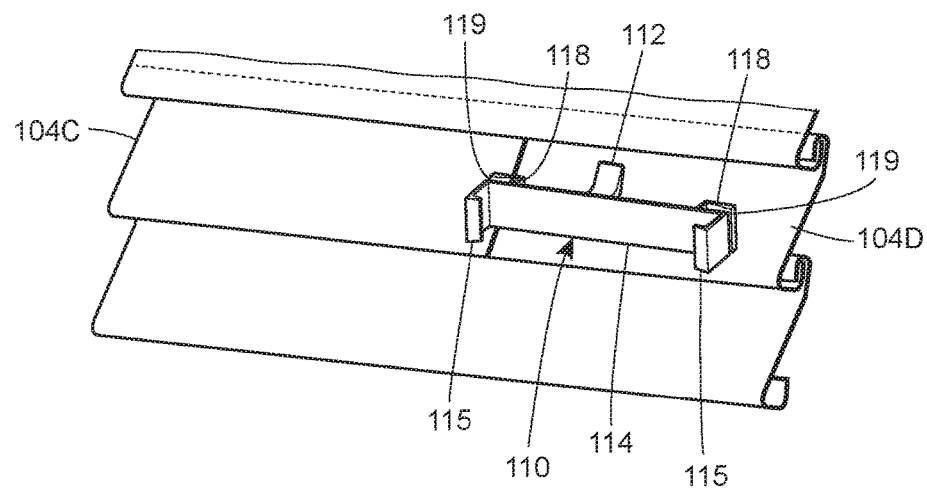

FIGS. 6A and 6B illustrate perspective views of the siding evaluation apparatus 110 removably attached to building siding 104. These figures illustrate the exemplary siding evaluation apparatus 110 of FIG. 5 without the color chart 116, which representation is for the sake of clarity only and is not intended to be limiting. The dashed lines within these FIGS. 6A and 6B represent obscured or covered portions, including overlapped portions of the building siding 104 and portions of the protrusion 112 and clip 118 obscured by the building siding 104. Although the building siding 104 may be attached to a wall 102, the wall is also not illustrated for the sake of clarity. In the manner described below, the siding evaluation apparatus 110 may be removably attached or secured to the building siding 104. Moreover, the siding evaluation apparatus 110 may be removably attached or secured to a plurality of portions of building siding of one or more buildings at different times.

As illustrated in FIG. 6A, the protrusion 112 may be inserted between overlapping segments of the building siding 104. The tapered portion 113 of the protrusion 112 is illustrated as being inserted or wedged between a top row 104A and a bottom row 104B of the building siding 104. The top row 104A overlaps a portion of the bottom row 104B, with or without a gap between them. When a portion of the protrusion 112 is inserted under the overlapping portion of the top row 104A and over the overlapped portion of the bottom row 104B, the protrusion 112 wedges between the rows. Thus, the insertion of the protrusion 112 between the rows 104A and 104B creates pressure upon the protrusion 112 and the rows 104A and 104B. This pressure then holds the siding evaluation apparatus 110 in place by friction between the protrusion 112 and the rows 104A and 104B of the building siding 104. While the siding evaluation apparatus 110 is thus held in place relative to the building siding 104, the color chart holder 114 may hold the color chart 116 (not shown) to be displayed in proximity to at least a portion of the building siding 104. The color chart 116, thus held in place by the color chart holder 114, may be photographed using the camera 106 or other image capture device. Additionally, or alternatively, the color chart 116 may be used for calibration or comparison purposes without being photographed. When the color chart 116 is no longer needed, the siding evaluation apparatus 110 may be removed by pulling the siding evaluation apparatus 110 to dislodge the protrusion 112 from between the top row 140A and the bottom row 104B of the building siding 104.

As illustrated in FIG. 6B, one of the clips 118 may receive a portion of the building siding 104 to removably attach the siding evaluation apparatus 110 to the building siding 104. The clip 118 may receive a portion of the building siding 104 at a seam between two segments. In the illustrated embodiment, the seam between segment 104C and segment 104D of the building siding 104 includes a portion where the segment 104C overlaps segment 104D within the same row. In other embodiments, the building siding 104 may include non-overlapping seams. As shown, the clip 118 is positioned around a portion of the segment 104C at the seam, such that the portion of segment 104C is received into the gap between the clip 118 and the back face of the color chart holder 114. When the segment 104C is thus inserted into the clip 118, the tension in the clip 118 generates pressure, which is applied to the segment 104C at the pressure point 119. This pressure holds the siding evaluation apparatus 110 in place relative to the building siding 104. As discussed above, the color chat holder 114 may hold the color chart 116 (not shown) in place to be photographed with at least a portion of the building siding 104. When the color chart 116 no longer needs to be held in place, the siding evaluation apparatus 110 may be removed by applying a force to slide the clip 118 off of the received portion of the segment 104C to decouple the siding evaluation apparatus 110 from the segment 104C of the building siding 104.

Figure 7:
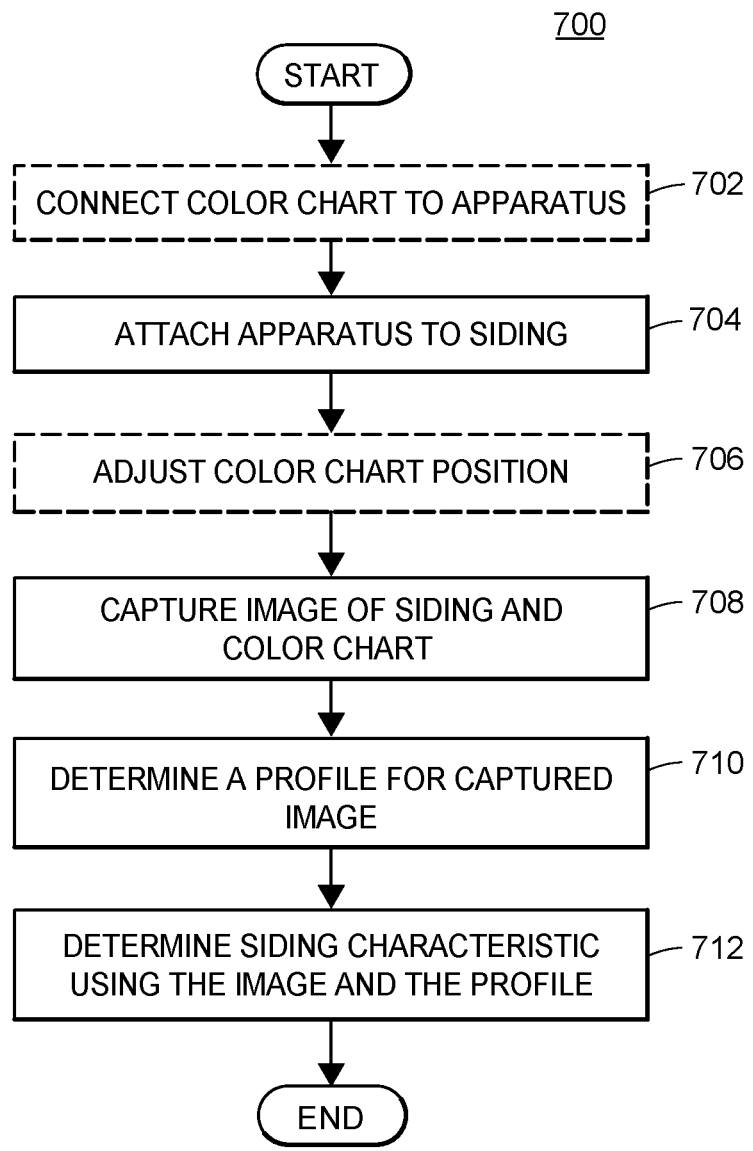
FIG. 7 illustrates a flow diagram of an exemplary method of using the siding evaluation apparatus in determining a characteristic of the building siding.

FIG. 7 illustrates a flow diagram of an exemplary method 700 for using the siding evaluation apparatus 110 in determining a characteristic of the building siding 104. The method 700 may begin at block 702, in some embodiments, with connecting the color chart 116 to the color chart holder 114. Otherwise, the method 700 may begin at block 704 with attaching the siding evaluation apparatus 110 to the building siding 104, as discussed above. In embodiments in which the color chart 116 may be positioned or adjusted using the adjustable connector 111, the position of the color chart 116 may be adjusted at block 706. At block 708, the camera 106 or other image capture device may be used to capture an image of the color chart 116 and at least a portion of the building siding 104. At block 710, the captured image may be processed by the computing device 140 to determine a profile for the captured image. One or more characteristics of the building siding 104 may then be determined by the computing device 140, using the determined profile and the captured image. Blocks 702 and 706 may occur in another order than the order described with respect to the exemplary method 700. For example, the color chart 116 may be connected to the color chart holder 114 before or after the siding evaluation apparatus 110 is attached to the building siding 104.

At block 702, the color chart 116 may be attached to the color chart holder 114 in embodiments in which the color chart 116 does not form an integral part of the color chart holder 114. This may be achieved using the hooks 115 or other connecting portions of the color chart holder 114, as discussed above. In embodiments in which the color chart 116 is not readily removable from the color chart holder 114, such as the embodiment illustrated in FIGS. 2A-D, the block 702 may be unnecessary.

At block 704, the siding evaluation apparatus 110 is removably attached to a portion of the building siding 104, as discussed above. The attachment is made in a manner such that the siding evaluation apparatus 110 is held in place relative to the building siding 104 by pressure or friction, as discussed above. The attachment may be made by any means discussed herein, particularly by insertion of the protrusion 112 between overlapping segments of the building siding 104 or by clipping the clip 118 onto a portion of a seam of the building siding 104.

At block 706, the position of the color chart 116 may be adjusted, in some embodiments. When the siding evaluation apparatus 110 includes the adjustable connector 111, the position of the color chart 116 relative to the building siding 104 may be adjusted. In some embodiments, the color chart 116 may be adjusted to be substantially parallel to at least a portion of the building siding 104, thereby facilitating image capture of the color chart 116 together with at least a portion of the building siding 104. Adjusting the position of the color chart 116 may include adjusting the position of the color chart holder 114 relative to the protrusion 112, clip 118, or other means of removably attaching the siding evaluation apparatus to the building siding 104. For example, in embodiments in which the adjustable connector 111 is disposed between the color chart holder 114 and the protrusion 112 or clip 118, the siding evaluation apparatus 110 may be adjusted so that the entire color chart 116 and the color chart holder 114 may be repositioned relative to the protrusion 112 or clip 118. In embodiments in which the adjustable connector is disposed within one of the protrusion 112, the color chart holder 114, or the clip 118, the adjustment may similarly be made, but such adjustment may not result in a relative change of position between some components or portions of components of the siding evaluation apparatus 110. In further embodiments, a plurality of adjustable connectors may be included within the siding evaluation apparatus 110, thereby facilitating multiple ways of adjusting the position of the color chart 116.

At block 708, the camera 106 or other image capture device may be used to capture one or more images of the color chart 116 and at least a portion of the siding 104. In preferred embodiments, this includes capturing at least one digital image that includes both the color chart 116 and the portion of the building siding 104. Some embodiments may include multiple images, some of which may not include the color chart 116. For example, the color chart 116 may be captured in a first image in order to provide a scale or color reference, which may be carried over from the first captured image to another captured image. As another example, the color chart 116 may be used to adjust the camera 106 or other image capture device at the time the images are taken, such that it is not captured in any or all of the images. In most embodiments, the siding evaluation apparatus 110 will obscure at least some of the portion of the building siding 104 to which the siding evaluation apparatus 110 is removably attached, so the portion of the building siding 104 captured in the image may include a further portion of the building siding 104 that is in close proximity to the point of attachment of the siding evaluation apparatus 110. In preferred embodiments, the image may be captured as a digital image in order to facilitate further processing.

At block 710, the computing device 140 may process information associated with the color chart 116 to determine a profile for the one or more captured images. One or more modules stored within the program memory 146 may be executed by the one or more processors 142 of the computing device 140 to receive and process the captured image. When the captured image includes at least a portion of the color chart 116, the profile may be determined using at least a portion of the color chart 116 within the captured image. For example, a scale indicating a known distance that is included in the color chart 116 may be identified within the captured image. The identified scale may then be used to determine distances in one or more dimensions within the captured image. The distances may be translated into or used to determine a profile for the captured image that indicates distances in a desired measurement system (e.g., millimeters or inches) within the captured image. Such profile may include one or more distance values associated with each pixel dimension. For example, the profile may indicated that each pixel in the image has been determined to have an equivalent distance value of 0.2 millimeters in the horizontal direction and 0.3 millimeters in the vertical direction, based upon a known scale or other portion of the color chart 116. As another example, one or more patches of known color may be identified within the color chart 116 in the captured image and used to determine a color profile for the captured image. This may include adjusting one or more aspects of the colors of pixels within the captured image to adjust for differences between cameras or lighting conditions.

At block 712, the computing device 140 may determine one or more characteristics of the building siding 104 based upon the one or more captured images and the determined profile or profiles associated with the one captured images. Again, one or more modules stored within the program memory 146 may be executed by the one or more processors 142 of the computing device 140 to determine the one or more characteristics of the building siding 104. The one or more characteristics of the building siding 104 may include the following: a size associated with the building siding, a condition of the building siding, an age of the building siding, or damage to the building siding. For example, the size of the siding may be determined based upon distance information identified in the profile based upon a portion of the color chart 116. The size dimensions may further be used to determine a type of the building siding 104, which may include a general category of siding, as well as one or more possible brands or models of siding that match the size characteristics of the building siding 104. In some embodiments, a color of the building siding 104 may be determined by appropriate adjustment of the captured image and the profile determined from the color chart 116. This information may be used to determine an appropriate color for replacement siding in order to match both the type and color of the building siding 104. This may be particularly useful where the building siding 104 has substantial weathering that has altered the color of the siding from its initial color. As yet another example, the captured image may be processed with the profile information to determine a material type of the building siding 104. For example, the profile may indicate reflectivity information allowing a determine of the level of reflection off the building siding 104, which may indicate the material of which the siding is made. For example, vinyl siding may be less reflective (or less glossy) than aluminum siding. By using known information from the color profile 116 to correct for differences in scale and environmental conditions, the characteristics discussed above or others may be determined for the building siding, either automatically or with human assessment. When automatically determined, the captured image may be processed by one or more processors of a computing device, which may include using machine learning techniques, such as support machine vectors (SMV), neural networks, or random forest analysis.

Blocks 710 and 712 of the exemplary method 700 or other similar methods may be performed by one or more modules of the computing device 140 executed by the one or more processors 142. In some embodiments, the computing device 140 may be disposed within the camera 106 or other image capture device, which may include a tablet computer or smartphone. In other embodiments, the computing device 140 may be a separate device configured to receive the captured image, which device may be a general purpose or special purpose computer, including desktop, notebook, tablet, mobile, or wearable computing devices.

Additional Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or siding evaluation apparatus that comprises a list of elements is not necessarily limited to only those elements but may include other elements not expressly listed or inherent to such process, method, article, or siding evaluation apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

Upon reading this disclosure, those of skill in the art will appreciate still additional alternative structural and functional designs for system and a method for assigning mobile device data to a vehicle through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and siding evaluation apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A siding evaluation apparatus for use in identifying a characteristic of building siding, comprising: means for removably attaching the siding evaluation apparatus to a first portion of the building siding using at least one of pressure or friction; and a color chart holder adapted to hold a color chart in a manner such that the color chart and a second portion of the building siding are simultaneously visible when the siding evaluation apparatus is attached to the first portion of the building siding.

2. The siding evaluation apparatus according to aspect 1, wherein the means for removably attaching the siding evaluation apparatus to the first portion of the building siding includes a protrusion adapted to be removably inserted between rows of siding to hold the siding evaluation apparatus in place.

3. The siding evaluation apparatus according to aspect 2, wherein the protrusion includes a tapered portion that is tapered to be thinner at an end of the protrusion extending away from the color chart holder.

4. The siding evaluation apparatus according to either of aspect 2 or aspect 3, wherein: the tapered portion has a thin end away from the color chart holder and a thick end nearer the color chart holder; the thin end has a thickness less than 2 millimeters; and the thick end has a thickness greater than 2 millimeters.

5. The siding evaluation apparatus according to any one of aspects 1-4, wherein the means for removably attaching the siding evaluation apparatus to the first portion of the building siding includes a clip adapted to receive the first portion of the building siding to hold the siding evaluation apparatus in place.

6. The siding evaluation apparatus according to aspect 5, wherein the clip receives a portion of a seam of the building siding.

7. The siding evaluation apparatus according to either of aspect 4 or aspect 5, wherein the clip includes a gap between 0.3 and 3 millimeters into which the first portion of the building siding is received.

8. The siding evaluation apparatus according to any one of aspects 1-7, wherein the color chart holder includes one or more hooks to connect to one or more of the color chart or a color chart case containing the color chart.

9. The siding evaluation apparatus according to any one of aspects 1-8, wherein the means for removably attaching the siding evaluation apparatus to the first portion of the building siding and the color chart holder form a single piece of one of the following: synthetic plastic, rubber, or solid resin.

10. The siding evaluation apparatus according to any one of aspects 1-9, further comprising an adjustable connector disposed between the means for removably attaching the siding evaluation apparatus to the first portion of the building siding and the color chart holder, which adjustable connector is adapted to rotate or slide the color chart holder in relation to the position of the means for removably attaching the siding evaluation apparatus to the first portion of the building siding.

11. A system for identifying a characteristic of building siding, comprising: a siding evaluation apparatus adapted to removably attach to a first portion of the building siding and further adapted to hold a color chart for display in proximity to the first portion of the building siding; a color chart; an image capture device positioned to capture an image of the color chart; a computing device communicatively connected to the image capture device, including one or more processors and a module stored in a program memory of the computing device that, when executed by the one or more processors, cause the computing device to: receive a digital image of the color chart and a second portion of the siding from the image capture device, and determine a characteristic of the building siding based upon the received digital image.

12. The system according to aspect 11, wherein the siding evaluation apparatus is adapted to removably attach to the first portion of the building siding by one or more of the following: a protrusion adapted to be removably inserted between rows of siding to hold the siding evaluation apparatus in place or a clip adapted to receive the first portion of the building siding to hold the siding evaluation apparatus in place.

13. The system according to either of aspect 10 or aspect 11, wherein: the color chart includes one or more known reference areas; and module further causes the computing device to adjust a color profile of the digital image based upon the one or more known reference areas of the color chart.

14. The system according to any one of aspects 11-13, wherein the color chart is removably connected to the siding evaluation apparatus.

15. A method for identifying a characteristic of building siding, comprising: removably attaching a siding evaluation apparatus to a first portion of the building siding, wherein the siding evaluation apparatus includes a color chart holder adapted to hold a color chart and a connecting portion adapted to hold the siding evaluation apparatus in place by one or more connectors; capturing an image of the color chart and a second portion of the building siding using an image capture device; determining, by one or more processors, a profile for the image based upon a portion of the captured image corresponding to at least a portion of the color chart; and determining, by one or more processors, a characteristic of the building siding based upon the captured image and the determined profile.

16. The method according to aspect 15, wherein the one or more connectors include at least one of the following: a protrusion adapted to be removably inserted between rows of siding to hold the siding evaluation apparatus in place or a clip adapted to receive the first portion of the building siding to hold the siding evaluation apparatus in place.

17. The method according to aspect 16, wherein the protrusion includes a tapered portion that is tapered to be thinner at the end of the protrusion away from the color chart holder and wherein the tapered portion has a thin end away from the color chart holder with a thickness less than 2 millimeters and a thick end nearer the color chart holder with a thickness greater than 2 millimeters.

18. The method according to either of aspect 16 or aspect 17, wherein the clip receives a portion of a seam of the building siding and wherein the clip includes a gap between 0.3 and 3 millimeters into which the portion of the seam is received.

19. The method according to any one of aspects 15-18, wherein determining the characteristic of the building siding includes determining at least one of the following: a size associated with the building siding, a condition of the building siding, an age of the building siding, or damage to the building siding.

20. The method according to any one of aspects 15-19, further comprising: adjusting the position of the color chart holder to display the color chart substantially parallel to the second portion of the building siding by adjusting the position of an adjustable connector between the color chart holder and the connecting portion.

What is claimed is:

1. A siding evaluation apparatus for use in identifying a characteristic of building siding, comprising:
   means for removably attaching the siding evaluation apparatus to a first portion of the building siding using at least one of pressure or friction; and
   a color chart holder adapted to hold a color chart in a manner such that the color chart and a second portion of the building siding are simultaneously visible when the siding evaluation apparatus is attached to the first portion of the building siding.

2. The siding evaluation apparatus of claim 1, wherein the means for removably attaching the siding evaluation apparatus to the first portion of the building siding includes a protrusion adapted to be removably inserted between rows of siding to hold the siding evaluation apparatus in place.

3. The siding evaluation apparatus of claim 2, wherein the protrusion includes a tapered portion that is tapered to be thinner at an end of the protrusion extending away from the color chart holder.

4. The siding evaluation apparatus of claim 3, wherein:
   the tapered portion has a thin end away from the color chart holder and a thick end nearer the color chart holder;
   the thin end has a thickness less than 2 millimeters; and
   the thick end has a thickness greater than 2 millimeters.

5. The siding evaluation apparatus of claim 1, wherein the means for removably attaching the siding evaluation apparatus to the first portion of the building siding includes a clip adapted to receive the first portion of the building siding to hold the siding evaluation apparatus in place.

6. The siding evaluation apparatus of claim 5, wherein the clip receives a portion of a seam of the building siding.

7. The siding evaluation apparatus of claim 5, wherein the clip includes a gap between 0.3 and 3 millimeters into which the first portion of the building siding is received.

8. The siding evaluation apparatus of claim 1, wherein the color chart holder includes one or more hooks to connect to one or more of the color chart or a color chart case containing the color chart.

9. The siding evaluation apparatus of claim 1, wherein the means for removably attaching the siding evaluation apparatus to the first portion of the building siding and the color chart holder form a single piece of one of the following: synthetic plastic, rubber, or solid resin.

10. The siding evaluation apparatus of claim 1, further comprising an adjustable connector disposed between the means for removably attaching the siding evaluation apparatus to the first portion of the building siding and the color chart holder, which adjustable connector is adapted to rotate or slide the color chart holder in relation to the position of the means for removably attaching the siding evaluation apparatus to the first portion of the building siding.

11. A system for identifying a characteristic of building siding, comprising:
a siding evaluation apparatus adapted to removably attach to a first portion of the building siding and further adapted to hold a color chart for display in proximity to the first portion of the building siding;
a color chart;
an image capture device positioned to capture an image of the color chart; and
a computing device communicatively connected to the image capture device, including one or more processors and a module stored in a program memory of the computing device that, when executed by the one or more processors, cause the computing device to:
receive a digital image of the color chart and a second portion of the siding from the image capture device; and
determine a characteristic of the building siding based upon the received digital image.

12. The system of claim 11, wherein the siding evaluation apparatus is adapted to removably attach to the first portion of the building siding by one or more of the following: a protrusion adapted to be removably inserted between rows of siding to hold the siding evaluation apparatus in place or a clip adapted to receive the first portion of the building siding to hold the siding evaluation apparatus in place.

13. The system of claim 11, wherein:
the color chart includes one or more known reference areas; and
module further causes the computing device to adjust a color profile of the digital image based upon the one or more known reference areas of the color chart.

14. The system of claim 11, wherein the color chart is removably connected to the siding evaluation apparatus.

15. A method for identifying a characteristic of building siding, comprising:
removably attaching a siding evaluation apparatus to a first portion of the building siding, wherein the siding evaluation apparatus includes a color chart holder adapted to hold a color chart and a connecting portion adapted to hold the siding evaluation apparatus in place by one or more connectors;
capturing an image of the color chart and a second portion of the building siding using an image capture device;
determining, by one or more processors, a profile for the image based upon a portion of the captured image corresponding to at least a portion of the color chart; and
determining, by one or more processors, a characteristic of the building siding based upon the captured image and the determined profile.

16. The method of claim 15, wherein the one or more connectors include at least one of the following: a protrusion adapted to be removably inserted between rows of siding to hold the siding evaluation apparatus in place or a clip adapted to receive the first portion of the building siding to hold the siding evaluation apparatus in place.

17. The method of claim 16, wherein the protrusion includes a tapered portion that is tapered to be thinner at the end of the protrusion away from the color chart holder and wherein the tapered portion has a thin end away from the color chart holder with a thickness less than 2 millimeters and a thick end nearer the color chart holder with a thickness greater than 2 millimeters.

18. The method of claim 16, wherein the clip receives a portion of a seam of the building siding and wherein the clip includes a gap between 0.3 and 3 millimeters into which the portion of the seam is received.

19. The method of claim 15, wherein determining the characteristic of the building siding includes determining at least one of the following: a size associated with the building siding, a condition of the building siding, an age of the building siding, or damage to the building siding.

20. The method of claim 15, further comprising:
adjusting the position of the color chart holder to display the color chart substantially parallel to the second portion of the building siding by adjusting the position of an adjustable connector between the color chart holder and the connecting portion.

* * * * *